United States Patent [19]

Collins et al.

[11] 3,933,837

[45] Jan. 20, 1976

[54] 3,4-METHYLENEDIOXYPHENOXY-ALKYL DIKETONES AND KETO-ESTERS

[75] Inventors: Joseph C. Collins, East Greenbush; Guy D. Diana, Stephentown, both of N.Y.

[73] Assignee: Sterling Drug Inc., New York, N.Y.

[22] Filed: July 23, 1973

[21] Appl. No.: 381,406

[52] U.S. Cl............................. 260/340.5; 424/282
[51] Int. Cl.²........................................ C07D 317/06
[58] Field of Search................................. 260/340.5

[56] References Cited
UNITED STATES PATENTS 3,686,222   8/1972   Chodnekar et al............. 260/340.5
3,787,443   1/1974   Erickson........................ 260/340.5

*Primary Examiner*—V. D. Turner
*Attorney, Agent, or Firm*—Thomas L. Johnson; B. Woodrow Wyatt

[57] ABSTRACT

Aryloxyalkyl diketones and keto-esters, having pesticidal and anti-viral activity, are prepared from an aryloxyalkyl halide and an alkali metal enolate salt of a diketone or keto-ester.

10 Claims, No Drawings

3,4-METHYLENEDIOXYPHENOXY-ALKYL DIKETONES AND KETO-ESTERS

This invention relates to aryloxyalkyl diketone and keto-esters, to the preparation thereof and to compositions and methods for the use thereof.

The compounds of the invention are of the structural formula

I wherein:
- Alk is alkylene of 3 to 10 carbon atoms and having 3 to 7 carbon atoms intervening between the terminal bonds;
- R is alkanoyl of 2 to 6 carbon atoms;
- R' is alkanoyl of 2 to 6 carbon atoms or carboalkoxy of 2 to 6 carbon atoms;
- and Ar is phenyl substituted by 3,4-methylenedioxy.

In the above general formula I, Alk stands for a saturated aliphatic hydrocarbon bridge containing from 3 to 12 carbon atoms such that the O atom and the R'RCH moiety are separated by from 3 to 7 carbon atoms. Thus the alkylene bridge may be straight or branched, and must be branched if it contains more than seven carbon atoms. A preferred class of compounds are those where Alk is straight chain alkylene of 3 to 7 carbon atoms, and if the Alk bridge is branched, it is preferred that it be symmetrical, that is with the branching at the same relative positions from either end of the bridge.

The carbon chains of R and R' can be straight or branched, although primary or secondary alkyl moieties are preferred.

The compounds of the invention are prepared according to the following reaction sequence:

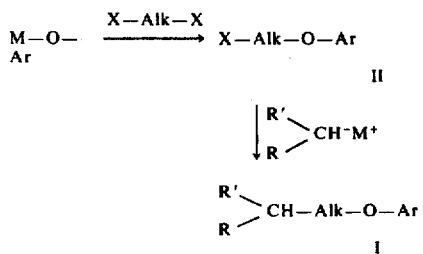

An alkali metal salt of a phenol (HOAr), M—Y—Ar, where M is alkali metal, preferably sodium or potassium, is interacted with an alkylene dihalide, X—Alk—X, where X is bromine or iodine. The reaction takes place with moderate heating, between about 50° and 100°C. in an inert solvent using equimolar quantities of reactants, or preferably a stoichiometric excess of dihalide to minimize di-ether (Ar—O—Alk—O—Ar) formation. The di-ether that is formed is readily separated from the desired mono-ether (II), because the former is a relatively high melting solid which separates readily from organic solvents while the mono-ether remains in solution.

It is preferred to carry out the initial etherification step with a dibromide (X—Alk—X where X is Br) because of the more ready availability of dibromides as compared to diiodides. The resulting aryloxyalkyl bromide (X—Alk—O—Ar where X is Br) can be interacted directly with the alkali metal enolate salt RR'λCH⁻M⁺, or if desired converted to the corresponding iodide (X—Alk—O—Ar where X is I) which reacts somewhat more easily with the enolate salt than does the bromide. The conversion of II (X = Br) to II (X = I) is effected by heating the former with sodium or potassium iodide in an inert solvent, e.g. acetone.

The dihalides, X—Alk—X, where Alk is branched are preferably symmetrical, that is, the branching is in the same relative position or positions with respect to the terminal halogen atoms, in order to avoid production of mixtures upon ether formation.

It is also possible to employ chlorobromoalkanes as the dihalide reactant, namely, Cl—Alk—Br. The use of such mixed dihalides has the advantage that di-ether formation is eliminated or minimized, since reaction occurs almost exclusively with the bromine atom, especially if stoichiometric proportions of phenol and dihalide are used. Furthermore, it is possible by this variation in the procedure to obtain compounds with unsymmetrically branched alkylene bridges without producing mixtures. The resulting chloroalkoxy aryl ether, Cl—Alk—O—Ar, must then be converted to the corresponding bromoalkoxy aryl ether or iodoalkoxy aryl ether before it will react with the alkali metal enolate salt of a diketone or keto-ester. The chlorobromoalkane starting materials can be prepared by reduction, e.g. with lithium aluminum hydride, of a chloro-ester, Cl—Alk'—COOCH₃, to afford a chloroalkanol, Cl—Alk—OH, followed by replacement of the hydroxy group with bromine, e.g. with phosphorus tribromide.

In the final step, the mono-ether, X—Alk—O—Ar (II), is treated with the alkali metal enolate salt of a diketone or keto-ester of formula RR'CH⁻M⁺, where R and R' have the meanings given hereinabove and M⁺ is an alkali metal cation, preferably lithium. The reaction takes place in an inert solvent under anhydrous conditions at ambient temperature or slightly above (25°–70°C.).

Biological evaluation of the compounds of the invention has shown that they possess antiviral activity. They have been found to be effective in vitro against one or more of a variety of viruses, including rhino-2, equine rhino, human rhino, para-influenza, herpes and respiratory syncitial virus at minimal growth inhibitory concentrations (mic) ranging from about 0.5 to about 50 micrograms per milliliter. The mic values were determined by standard serial dilution procedures.

The compounds of the invention also possess pesticidal activity against arthropod species, as indicated by tests under simulated field conditions in a greenhouse against one or more of the following pest species: yellow mealworm pupae, alfalfa weevil larvae and yellow fever mosquito larvae.

The structures of the compounds of the invention were established by the modes of synthesis, by elementary analysis, and by infrared and nuclear magnetic resonance spectral determinations.

A further aspect of the invention relates to compositions for combatting arthropods by hindering the maturation thereof which comprise an effective amount of at least one compound of formula I in admixture with a suitable carrier or diluent, and to the method of combatting arthropods at any stage of their development by contacting them with said compositions.

The compositions of the invention are effective against insects at any stage of their development short of the final adult form, i.e. at the egg, larval or pupal stages. The compounds can be formulated in conventional manner as solutions, emulsions, suspensions, dusts and aerosol sprays. The pesticide compositions of the invention can contain adjuvants found normally in such preparations, including water and/or organic solvents such as acetone, dimethylformamide, sesame oil, petroleum oils, and the like. Emulsifying and surface active agents may also be added. Dust formulations can contain talc, diatomaceous earth, kaolin, bentonite, calcium carbonate, wood, flour, cork, carbon, and the like. The aerosol sprays contain propellants such as dichlorodifluoromethane. The compounds of this invention can be employed as the sole pesticide component or they can be used in admixture with other compounds having similar utility. While the concentration of active ingredient can vary within rather wide limits, ordinarily the pesticide will comprise not more than about 10%, and preferably about 1% by weight of the composition.

A still further aspect of the invention relates to compositions for combatting viruses which comprise an anti-virally effective amount of at least one compound of formula I in admixture with a suitable carrier or diluent, and to the method of combatting viruses by contacting the locus of said viruses with said compositions.

The antiviral compositions are formulated by preparing a dilute solution or suspension in an organic or aqueous-organic medium, for example ethyl alcohol, acetone, dimethylsulfoxide, and the like; and are applied to the locus to be disinfected by conventional means such as spraying, swabbing or immersing. Alternatively, the compounds can be formulated as ointments or creams by incorporating them in conventional ointment or cream bases, such as alkylpolyether alcohols, cetyl alcohol, stearyl alcohol and the like; as jellies by incorporating them in conventional jelly bases such as glycerin and tragacanth; or as aerosol sprays or foams.

The following examples will further illustrate the invention.

EXAMPLE 1 a. 4-(3,4-Methylenedioxyphenoxy)butyl bromide.

3,4-Methylenedioxyphenol (sesamol) (13.8 g., 0.1 mole) was dissolved in 100 ml. of 1N sodium hydroxide, and the solution was filtered and concentrated in vacuo to remove the water. The residue was digested with ether and dried in vacuo at 40°C. for 5 hours. A mixture of 10 g. (0.062 mole) of the resulting sodium salt of 3,4-methylenedioxyphenol and 21 g. (0.1 mole) of 1,4-dibromobutane in 75 ml. of dimethylformamide was stirred at 60°C. for about 16 hours under nitrogen. The reaction mixture was concentrated in vacuo to remove the solvent and the residue extracted with 150 ml. of methylene dichloride. The solid sodium bromide was removed by filtration, and the filtrate was washed with dilute sodium bicarbonate and with water, dried over anhydrous magnesium sulfate and concentrated to remove the solvent. The residual oil was crystallized from 50 ml. of 95% ethanol to give 9.5 g. of 4-(3,4-methylenedioxyphenoxy)butyl bromide, m.p. 52°–54°C.

b. 4-[4-(3,4-Methylenedioxyphenoxy)butyl]-3,5-heptanedione

[I; Ar is 3,4-methylenedioxyphenyl, Alk is $CH_2CH_2CH_2CH_2$, R and R' are $CH_3CH_2CO$].

A mixture of 21 g. (0.15 mole) of the lithium salt of 3,5-heptanedione (prepared from 22.8 g. of 3,5-heptanedione in 300 ml. of ether, and 108 ml. of 1.6N butyllithium in hexane added dropwise over 30 minutes at $-15°$C.) and 26.1 g. of 4-(3,4-methylenedioxyphenoxy)butyl bromide in 200 ml. of dimethylformamide was stirred and heated at 52°–53°C. for 1 day under nitrogen. The reaction mixture was concentrated in vacuo to remove the solvent, and the residue was partitioned between ether and water. The ether layer was washed successively with 5% aqueous sulfuric acid, water, 5% aqueous sodium bicarbonate and water, and then concentrated to remove the solvent. The residue (25 g.) was chromatographed on a column of 400 g. of silica gel, applied in pentane:benzene 90:10 solution. The column was eluted with the pentane-benzene-chloroform solvent series, and the material (14.0 g.) brought out with benzene:chloroform 8:2 was rechromatographed on 240 g. of silica gel. The latter was eluted with the same solvent series, and pentane:benzene 80:20 to 50:50 brought out 8.0 g. of the desired product, 4-[4-(3,4-methylenedioxyphenoxy)butyl]-3,5-heptanedione.

Anal. Calcd. for $C_{18}H_{24}O_5$: C, 67.48; H, 7.55. Found: C, 67.71; H, 7.57.

IR (oil film) $\lambda_\mu$ $^{max}$ 3.42$ms$ + shldrs. (CH); 5.80$mss$, 5.90$s$ (C=O); 6.15$m$, 6.24$m$, 6.28$m$, 6.66$vs$, 6.73$vs$, 6.78$s$ + shldrs. (arom. + CH). Nuclear Magnetic Resonance (NMR) [20% $CDCl_3$, internal tetramethylsilane (TMS)] δppm (Ratio) 6.2–6.9(3) (arom.); 5.90(2) (O—$CH_2$—O); 3.5–4.1(3) (O$CH_2$, —CO—CH—CO—); 2.50(4) (CO—$CH_2$— x 2); 1.0–2.1(6) (—$CH_2$—C x 3); 1.05(6) (Me triplet x 2).

4-[4-(3,4-Methylenedioxyphenoxy)butyl]-3,5-heptanedione was found to be active pesticidally against yellow mealworm pupae, alfalfa weevil larvae and yellow fever mosquito larvae.

4-[4-(3,4-Methylenedioxyphenoxy)butyl]-3,5-heptanedione was found to have antiviral activity in vitro against equine rhino virus at a minimum effective concentration of 12 micrograms per milliliter.

By replacing the 1,4-dibromobutane in Example 1a by a molar equivalent amount of 1,3-dibromo-2-methylpropane or 1-bromo-3-(2-bromoethyl)octane, and proceeding with the subsequent steps of Example 1a and 1b, there can be obtained, respectively, 4-[3-(3,4-methylenedioxyphenoxy)-2-methylpropyl]-3,5-heptanedione [I; Ar is 3,4-methylenedioxyphenyl, Alk is $CH_2CH(CH_3)CH_2$, R and R' are $CH_3CH_2CO$], or 4-[5-(3,4-methylenedioxyphenoxy)-3-pentyl-pentyl]-3,5-heptanedione [I; Ar is 3,4-methylenedioxyphenyl, Alk is $CH_2CH_2CH(C_5H_{11})CH_2CH_2$, R and R' are $CH_3CH_2CO$].

By replacing the 3,4-methylenedioxyphenol in Example 1a by a molar equivalent amount of 4-fluorophenol, 4-bromophenol, 4-iodophenol, 2,4-dichlorophenol, 4-trifluoromethylphenol, 4-trifluoromethoxyphenol, 3,4-dibenzyloxyphenol or 3,4,5-trimethoxyphenol, and proceeding with the subsequent steps of Example 1a and 1b, there can be obtained, respectively, 4-[4-(4-fluorophenoxy)butyl]-3,5-heptanedione [I; Ar is 4-$FC_6H_4$, Alk is $CH_2CH_2CH_2CH_2$, R and R' are $CH_3CH_2CO$],
4-[4-(4-bromophenoxy)butyl]-3,5-heptanedione [I; Ar is 4-$BrC_6H_4$,
Alk is $CH_2CH_2CH_2CH_2$, R and R' are $CH_3CH_2CO$],
4-[4-(4-iodophenoxy)butyl]-3,5-heptanedione [I; Ar is 4-$IC_6H_4$,
Alk is $CH_2CH_2CH_2CH_2$, R and R' are $CH_3CH_2CO$],
4-[4-(2,4-dichlorophenoxy)butyl]-3,5-heptanedione [I; Ar is 2,4-$Cl_2C_6H_3$, Alk is $CH_2CH_2CH_2CH_2$, R and R' are $CH_3CH_2CO$],
4-[4-(4-trifluoromethylphenoxy)butyl]-3,5-heptanedione [I; Ar is 4-$F_3CC_6H_4$, Alk is $CH_2CH_2CH_2CH_2$, R and R' are $CH_3CH_2CO$],
4-[4-(4-trifluoromethoxyphenoxy)butyl]-3,5-heptanedione [I; Ar is 4-$F_3COC_6H_4$, Alk is $CH_2CH_2CH_2CH_2$, R and R' are $CH_3CH_2CO$],
4-[4-(3,4-dibenzyloxyphenoxy)butyl]-3,5-heptanedione [I; Ar is 3,4-$(C_6H_5CH_2O)_2C_6H_3$, Alk is $CH_2CH_2CH_2CH_2$, R and R' are $CH_3CH_2CO$],
or 4-[4-(3,4,5-trimethoxyphenoxy)butyl]-3,5-heptanedione [I; Ar is 3,4,5-$(CH_3O)_3C_3H_2$, Alk is $CH_2CH_2CH_2CH_2$, R and R' are $CH_3CH_2CO$].

By replacing the lithium salt of 3,5-heptanedione in Example 1b by a molar equivalent amount of the lithium salt of 2,4-pentanedione, 2,4-hexanedione, ethyl acetoacetate, ethyl 3-oxovalerate, ethyl 3-oxohexanoate or 6,8-tridecanedione, there can be obtained, respectively, 3-[4-(3,4-methylenedioxyphenoxy)butyl]-2,4-pentanedione [I; Ar is 3,4-methylenedioxyphenyl, Alk is $CH_2CH_2CH_2CH_2$, R and R' are $CH_3CO$],
3-[4-(3,4-methylenedioxyphenoxy)butyl]-2,4-hexanedione [I; Ar is 3,4-methylenedioxyphenyl, Alk is $CH_2CH_2CH_2CH_2$, R is $CH_3CO$, R' is $CH_3CH_2CO$],
ethyl 2-acetyl-6-(3,4-methylenedioxyphenoxy)hexanoate [I; Ar is 3,4-methylenedioxyphenyl, Alk is $CH_2CH_2CH_2CH_2$, R is $CH_3CO$, R' is $COOC_2H_5$],
ethyl 2-propionyl-6-(3,4-methylenedioxyphenoxy)hexanoate [I; Ar is 3,4-methylenedioxyphenyl, Alk is $CH_2CH_2CH_2CH_2$, R is $CH_3CH_2CO$, R' is $COOC_2H_5$],
ethyl 2-butyryl-6-(3,4-methylenedioxyphenoxy)hexanoate [I; Ar is 3,4-methylenedioxyphenyl, Alk is $CH_2CH_2CH_2CH_2$, R is $CH_3CH_2CH_2CO$, R' is $COOC_2H_5$] or
7-[4-(3,4-methylenedioxyphenoxy)butyl]-6,8-tridecanedione [I; Ar is 3,4-methylenedioxyphenyl, Alk is $CH_2CH_2CH_2CH_2$, R and R' are $CH_3(CH_2)_4CO$].

EXAMPLE 2 a. 5-(3,4-Methylenedioxyphenoxy)pentyl bromide.

A mixture of 27.6 g. (0.2 mole) of sesamol, 56 g. (0.4 mole) of potassium carbonate, 92 g. (0.4 mole) of 1,5-dibromopentane in 400 ml. of acetone was refluxed with stirring under nitrogen for 3 days. Part of the solvent (200 ml.) was distilled off, and 400 ml. of benzene and 200 ml. of water were added. The aqueous layer was separated and extracted with benzene. The combined organic layers were washed with 5% aqueous sodium bicarbonate and with water, dried over anhydrous magnesium sulfate and concentrated in vacuo. The residue of reddish oil was digested with 500 ml. of absolute ether, and the mixture was filtered to remove 5.0 g. of solid bis-ether, 1,5-bis(3,4-methylenedioxyphenoxy)pentane, m.p. 129°–130°C. The filtrate was evaporated and the residue distilled, b.p. 130°–135°C. (0.03–0.005 mm.) to give 30 g. of 5-(3,4-methylenedioxyphenoxy)pentyl bromide, m.p. 54°–57°C.

b. 5-[4-(3,4-Methylenedioxyphenoxy)pentyl]-3,5-heptanedione

[I; Ar is 3,4-methylenedioxyphenyl, Alk is $CH_2CH_2CH_2CH_2CH_2$, R and R' are $CH_3CH_2CO$]

was prepared from 30 g. of 5-(3,4-methylenedioxyphenoxy)pentyl bromide and 22 g. of the lithium salt of 3,5-heptanedione according to the procedure of Example 1b. The product was chromatographed on 800 g. of activated magnesium silicate and eluted with pentane containing increasing amounts of benzene to give 14 g. of 5-[4-(3,4-methylenedioxyphenoxy)pentyl]-3,5-heptanedione as a yellow oil.

Anal. Calcd. for $C_{19}H_{26}O_5$: C, 68.24; H, 7.84. Found: C, 68.00; H, 7.92.

IR (oil film) $\lambda_\mu^{max}$ 3.44mss + shldrs., 3.62m (CH); 5.81s, 5.91s (C=O), 6.16ms, 6.25mms, 6.33 shldr., 6.65–6.90vs, broad (arom. + CH).
NMR (20% $CDCl_3$, internal TMS) δppm (Ratio) 6.2–6.8(3) (arom.); 5.88(2) (O—$CH_2$—O); 3.4–4.0(3) ($OCH_2$, CO—CH—CO—); 2.5(4) (CO—$CH_2$— x 2); 1.0–2.0(8) (—C—$CH_2$ x 4); 1.02(6) (Me triplet × 2).

5-[4-(3,4-Methylenedioxyphenoxy)pentyl]-3,5-heptanedione was found to be active pesticidally against yellow mealworm pupae, alfalfa weevil larvae, and yellow fever mosquito larvae.

EXAMPLE 3 a. 7-(3,4-Methylenedioxyphenoxy)heptyl bromide was prepared from 27.6 g. of sesamol and 100 g. of 1,7-dibromoheptane in the presence of 53.8 g. of potassium carbonate in acetone according to the procedure of Example 2a. There was obtained 43.5 g. of 7-(3,4-methylenedioxyphenoxy)heptyl bromide, m.p. 45°–47°C.

b. 7-(3,4-Methylenedioxyphenoxy)heptyl iodide.

A mixture of 43.5 g. of 7-(3,4-methylenedioxyphenoxy)heptyl bromide, 20.7 g. of sodium iodide and 300 ml. of acetone was heated at reflux for 2 hours. The reaction mixture was filtered, the filtrate evaporated in vacuo, and the residue partitioned between water and methylene dichloride. The methylene dichloride layer was separated, washed with water, dried over anhydrous magnesium sulfate and concentrated. The residue comprising 7-(3,4-methylenedioxyphenoxy)heptyl iodide was used without further purification in the following reaction.

c.

4-[7-(3,4-Methylenedioxyphenoxy)heptyl]-3,5-heptanedione

[I; Ar is 3,4-methylenedioxyphenyl, Alk is $(CH_2)_7$, R and R' are $CH_3CH_2CO$] was prepared from 38.5 g. of 7-(3,4-methylenedioxyphenoxy)heptyl iodide and 22 g. of the lithium salt of 3,5-heptanedione according to the procedure of Example 1b. The product was chromatographed on 1000 g. of activated magnesium silicate and eluted with the pentane-benzene-chloroform solvent series. The chloroform eluants brought out 23.5 g. of 4-[7-(3,4-methylenedioxyphenoxy)heptyl]-3,5-heptanedione as a colorless solid.

Anal. Calcd. for $C_{21}H_{30}O_5$: C, 69.59; H, 8.34. Found: C, 69.63; H, 8.46.

IR (oil film) $\lambda_\mu$ $^{max}$ 3.44s + shldrs. (CH); 5.81mss, 5.91s (C=O); 6.16mms, 6.24 shldr., 6.33m, 6.66s, 6.72s, 6.75 shldr. (arom. and CH).

4-[7-(3,4-Methylenedioxyphenoxy)heptyl]-3,5-heptanedione was found to have antiviral activity against equine rhino virus at a minimum inhibitory concentration of 6 micrograms per milliliter.

According to the foregoing procedures starting from the appropriate substituted phenol and alkylene dibromide, the following compounds were prepared:

EXAMPLE 4

4-[6-(3,4-Methylenedioxyphenoxy)hexyl]-3,5-heptanedione

[I; Ar is 3,4-methylenedioxyphenyl, Alk is $(CH_2)_6$, R and R' are $CH_3CH_2CO$], light yellow oil, prepared from 6-(3,4-methylenedioxyphenoxy)hexyl bromide, m.p. 45°–46°C.

Anal. Calcd. for $C_{20}H_{28}O_5$: C, 68.94; H, 8.10. Found: C, 69.20; H, 8.12.

IR (oil film) $\lambda_\mu$ $^{max}$ 3.44s + shldrs. (CH), 5.81s, 5.91s (C=O); 6.16mms, 6.24 shldr., 6.33m, 6.67s, 6.73s, 6.79s + shldrs. (arom. and CH).

NMR (20% $CDCl_3$, internal TMS) δppm (Ratio) 6.1–6.8(3) (arom); 5.90(2) ($O-CH_2-O$); 3.5–4.0(3) ($O-CH_2$, $CO-CH-CO-$); 2.48(4) ($CO-CH_2 \times 2$); 1.0–2.2(10) ($C-CH_2 \times 5$); 1.03(6) (Me triplet × 2).

EXAMPLE 5

4-[3-(3,4-Methylenedioxyphenoxy)propyl]-3,5-heptanedione

[I; Ar is 3,4-methylenedioxyphenyl, Alk is $CH_2CH_2CH_2$, R and R' are $CH_3CH_2CO$], b.p. 179°–180°C. (0.05–0.1 mm.), viscous oil, prepared from 3-(3,4-methylenedioxyphenoxy)propyl bromide, m.p. 68°C.

Anal. Calcd. for $C_{17}H_{22}O_5$: C, 66.65; H, 7.24. Found: C, 66.82; H, 7.29.

IR (oil film) $\lambda_\mu$ $^{max}$ 3.43s + shldrs., 3.61m (CH); 5.81s, 5.90s (C=O); 6.16mms, 6.24m, 6.33m, 6.65–6.85s + shldrs. (arom. and CH).

We claim:
1. A compound of the formula

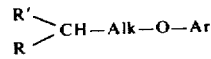

wherein:
Alk is alkylene of 3 to 10 carbon atoms and having 3 to 7 carbon atoms intervening between the terminal bonds;
R is alkanoyl of 2 to 6 carbon atoms;
R' is alkanoyl of 2 to 6 carbon atoms or carboalkoxy of 2 to 6 carbon atoms;
and Ar is phenyl substituted by 3,4-methylenedioxy.

2. A compound according to claim 1 wherein R and R' are alkanoyl of 2 to 6 carbon atoms.

3. A compound according to claim 1 wherein R and R' are alkanoyl of 2 to 6 carbon atoms and Alk is straight chain alkylene of 3 to 7 carbon atoms.

4. A compound according to claim 1 wherein R and R' are both propionyl and Alk is straight chain alkylene of 3 to 7 carbon atoms.

5. A compound according to claim 1 wherein R and R' are both propionyl, Alk is straight chain alkylene of 3 to 7 carbon atoms and Ar is 3,4-methylenedioxyphenyl.

6. 4-[4-(3,4-Methylenedioxyphenoxy)butyl]-3,5-heptanedione, according to claim 5.

7. 5-[4-(3,4-Methylenedioxyphenoxy)pentyl]-3,5-heptanedione, according to claim 5.

8. 4-[6-(3,4-Methylenedioxyphenoxy)hexyl]-3,5-heptanedione, according to claim 5.

9. 4-[3-(3,4-Methylenedioxyphenoxy)propyl]-3,5-heptanedione, according to claim 5.

10. 4-[7-(3,4-Methylenedioxyphenoxy)heptyl]-3,5-heptanedione, according to claim 5.

* * * * *

UNITED STATES PATENT AND TRADEMARK OFFICE
CERTIFICATE OF CORRECTION

PATENT NO. : 3,933,837
DATED : January 20, 1976
INVENTOR(S) : Joseph C. Collins and Guy D. Diana It is certified that error appears in the above-identified patent and that said Letters Patent are hereby corrected as shown below:

Column 6, lines 19-20; lines 30-31; lines 42-43;

and Column 8, lines 41-42, Claim 7, each instance:

"5-[4-(3,4-Methylenedioxyphenoxy)pentyl]-3,5-heptanedione"

should read --4-[5-(3,4-Methylenedioxyphenoxy)pentyl]-3,5-heptanedione--.

Signed and Sealed this

Third Day of May 1977

[SEAL]

Attest:

RUTH C. MASON
Attesting Officer

C. MARSHALL DANN
Commissioner of Patents and Trademarks